US008633976B2

(12) United States Patent
Yamaguchi et al.

(10) Patent No.: US 8,633,976 B2
(45) Date of Patent: Jan. 21, 2014

(54) POSITION SPECIFYING SYSTEM, POSITION SPECIFYING METHOD, AND COMPUTER READABLE MEDIUM

(75) Inventors: Hiroshi Yamaguchi, Kanagawa (JP); Kiyohiro Maeda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 879 days.

(21) Appl. No.: 12/328,402

(22) Filed: Dec. 4, 2008

(65) Prior Publication Data

US 2009/0147096 A1    Jun. 11, 2009

(30) Foreign Application Priority Data

Dec. 5, 2007    (JP) .................................. 2007-314497

(51) Int. Cl.
*A62B 1/04*    (2006.01)

(52) U.S. Cl.
USPC .......................................................... 348/65

(58) Field of Classification Search
USPC .......................................................... 348/65
IPC ....................................................... H04N 7/12
See application file for complete search history.

(56) References Cited

U.S. PATENT DOCUMENTS

| | | | | |
|---|---|---|---|---|
| 5,710,662 A | * | 1/1998 | Nishida | ......................... 359/368 |
| 6,464,633 B1 | * | 10/2002 | Hosoda et al. | ................. 600/178 |
| 2007/0156021 A1 | * | 7/2007 | Morse et al. | .................... 600/167 |

FOREIGN PATENT DOCUMENTS

| | | |
|---|---|---|
| JP | 08-322821 A | 12/1996 |
| JP | 2006-218013 A | 8/2006 |

* cited by examiner

*Primary Examiner* — David Czekaj
*Assistant Examiner* — Tracy Li
(74) *Attorney, Agent, or Firm* — Sughrue Mion, PLLC

(57) ABSTRACT

Provided is a position specifying system including: a light irradiation section that irradiates light to different positions of a physical body respectively; an image capturing section that captures images of an object existing inside the physical body, by means of the light irradiated to the different positions; and a position specifying section that specifies a depth of the object from a surface of the physical body onto which the light from the light irradiation section is irradiated, based on a difference in the images captured by the image capturing section.

16 Claims, 11 Drawing Sheets

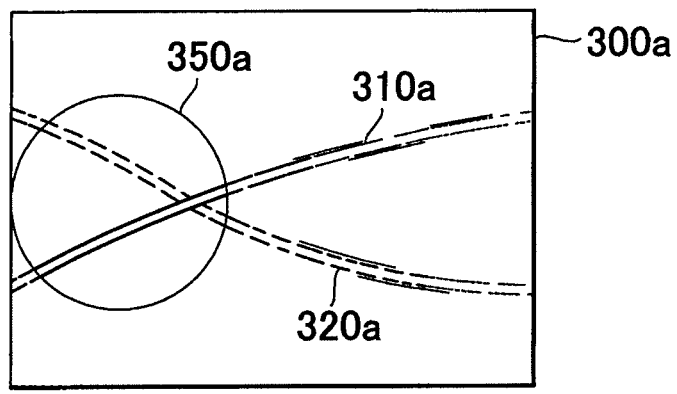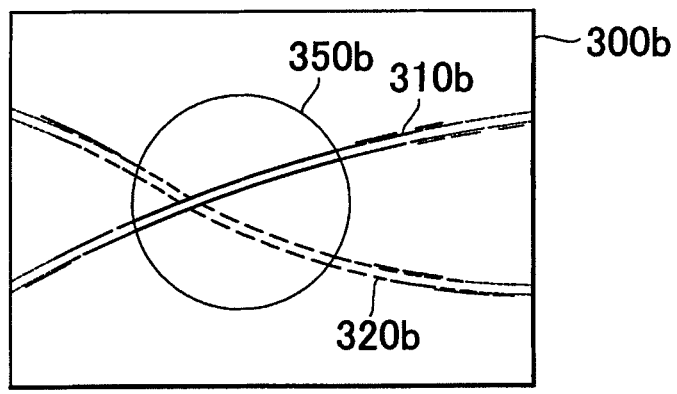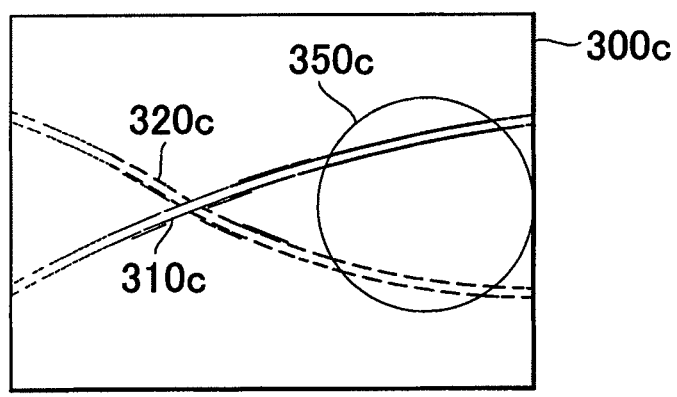
F I G . 3

POSITION SPECIFYING SYSTEM, POSITION SPECIFYING METHOD, AND COMPUTER READABLE MEDIUM

CROSS REFERENCE TO RELATED APPLICATION

This patent application claims priority from a Japanese patent application No. 2007-314497 filed on Dec. 5, 2007, the contents of which are incorporated herein by reference.

BACKGROUND

1. Technical Field

The present invention relates to a position specifying system, a position specifying method, and a computer readable medium. The present invention particularly relates to a position specifying system and a position specifying method for specifying a position of an object existing inside a physical body, and to a computer readable medium storing therein a program for the position specifying system.

2. Description of the Related Art

There is known a living organism information measuring apparatus for measuring living organism information in detail in response to the metabolism of the living organism by making use of the fact that the light propagation within a living organism is different for each wavelength of light, for example by Japanese Patent Application Publication No. 2006-218013. Moreover, there is known an optical measuring apparatus for obtaining an absorption coefficient distribution in the depth direction of a target analyte by measuring the absorbance between different incoming/outgoing points, for example by Japanese Patent Application Publication No. 8-322821.

With the technologies of Japanese Patent Application Publications Nos. 2006-218013 and 8-322821, the depth of an inside object cannot be calculated easily. For example, the both technologies necessitate measurement on different incoming/outgoing points is necessary, which prevents the internal state from being observed easily.

SUMMARY

In view of the above, according to an aspect of the innovations herein, provided is a position specifying system, a position specifying method, and a computer readable medium, which are capable of solving the above-stated problems. This object is achieved by combinations of features described in the independent claims. The dependent claims define further advantageous and concrete examples of the present invention.

According to an aspect of the innovations herein, provided is a position specifying system including: a light irradiation section that irradiates light to different positions of a physical body respectively; an image capturing section that captures images of an object existing inside the physical body, by means of the light irradiated to the different positions; and a position specifying section that specifies a depth of the object from a surface of the physical body onto which the light from the light irradiation section is irradiated, based on a difference in the images captured by the image capturing section.

According to an aspect of the innovations herein, provided is position specifying method including: irradiating light to different positions of a physical body respectively; capturing images of an object existing inside the physical body, by means of the light irradiated to the different positions; and specifying a depth of the object from a surface of the physical body onto which the light is irradiated in the light irradiating, based on a difference in the images captured in the image capturing.

According to an aspect of the innovations herein, provided is a computer readable medium storing thereon a program for a position specifying system, the program causing the position specifying system to function as: a light irradiation section that irradiates light to different positions of a physical body respectively; an image capturing section that captures images of an object existing inside the physical body, by means of the light irradiated to the different positions; and a position specifying section that specifies a depth of the object from a surface of the physical body onto which the light from the light irradiation section is irradiated, based on a difference in the images captured by the image capturing section.

The summary of the invention does not necessarily describe all necessary features of the present invention. The present invention may also be a sub-combination of the features described above.

BRIEF DESCRIPTION OF THE DRAWINGS

FIG. 3 shows an exemplary object image captured by an image capturing section 110.

DESCRIPTION OF EXEMPLARY EMBODIMENTS

The invention will now be described based on the preferred embodiments, which do not intend to limit the scope of the present invention, but exemplify the invention. All of the features and the combinations thereof described in the embodiment are not necessarily essential to the invention.

Figure 1:
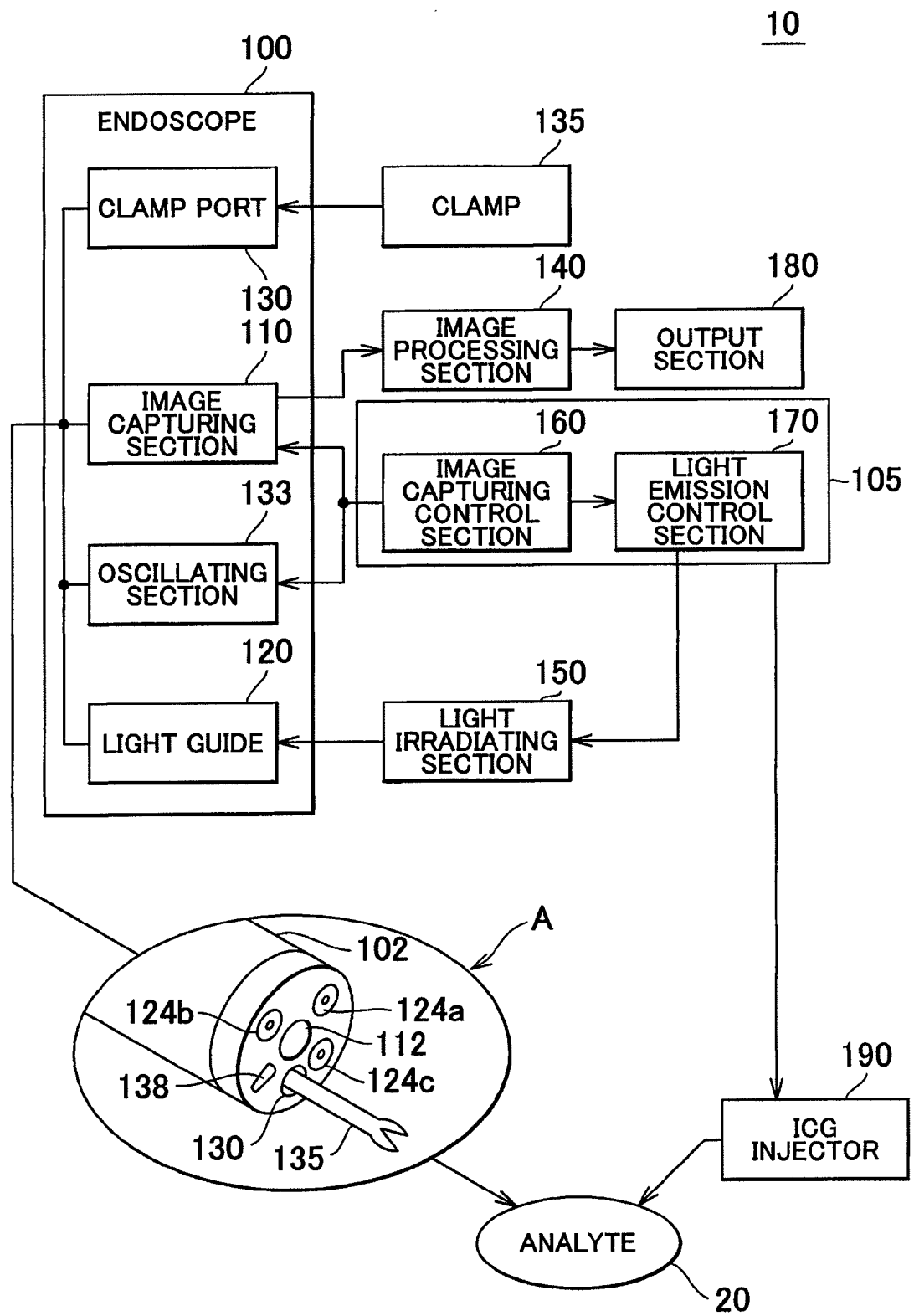
FIG. 1 shows an exemplary position specifying system 10 of the present embodiment, together with an analyte 20.

FIG. 1 shows an exemplary position specifying system 10 of the present embodiment, together with an analyte 20. The position specifying system 10 specifies a position of an object existing inside a physical body. The position specifying system 10 includes an endoscope 100, an image processing section 140, an output section 180, a light irradiation section 150, a control section 105, and an ICG injector 190. Note that FIG. 1 is an enlarged view of a tip 102 of the endoscope 100. The control section 105 includes an image capturing control section 160 and a light emission control section 170.

The ICG injector 190 injects indocyanine green (ICG) which is a luminescence substance, to the analyte 20 which is an example of a physical body in the present invention. Although ICG is used as the luminescence substance in the present embodiment, a fluorescent substance other than ICG may also be used as the luminescence substance. ICG emits fluorescence of a broad spectrum centering around 810 nm, by being excited by infrared light of a wavelength of 750 nm for example.

When the analyte 20 is a living organism, the ICG injector 190 injects ICG to the blood vessels of the living organism by means of intravenous injection. The position specifying system 10 captures the image of the blood vessels within the living organism using luminescence light from the ICG. Note that the luminescence light includes fluorescence and phosphor. Note that the luminescence light which is an example of light from a physical body includes luminescence light of chemical luminescence, triboluminescence, and thermal luminescence, other than light luminescence of excitation light.

The ICG injector 190 injects ICG to the analyte 20 so that the ICG concentration within the living organism is maintained substantially constant, by means of control performed by the control section 105 for example. Note that the analyte 20 may be a living organism such as a human body. Note that an object such as a blood vessel exists in the analyte 20. The position specifying system 10 according to the present embodiment detects the position (depth) of an object existing deeper than the surface of the analyte 20 that includes an inner surface of the organs or the like. Moreover, the position specifying system 10 corrects blurring occurred in the image of the object according to the detected position.

The endoscope 100 includes an image capturing section 110, a light guide 120, and a clamp port 130. The tip 102 of the endoscope 100 is provided with a lens 112 as part of the image capturing section 110. The tip 102 is also provided with outlets 124a-c as part of the light guide 120. The outlets 124-c are hereinafter occasionally collectively referred to as a outlet 124.

The light irradiation section 150 generates light to be irradiated from the tip 102 of the endoscope 100. The light generated by the light irradiation section 150 includes infrared light which is an example of excitation light capable of exciting the luminescence substance included in an object thereby emitting luminescence light, and irradiation light for irradiating the analyte 20. The irradiation light includes component light of R component, G component, and B component.

The light guide 120 is formed by an optical fiber for example. The light guide 120 guides light generated in the light irradiation section 150 to the tip 102 of the endoscope 100. The light generated in the light irradiation section 150 is irradiated onto the analyte 20 through the outlet 124. Note that the outlets 124a-c are able to irradiate light at different positions of the analyte 20 from the tip 102 of the endoscope 100. In the example of the present drawing, the outlets 124a-c are provided in different positions from each other. However, there may be a single outlet so that light is emitted therefrom to irradiate the different positions.

The image capturing section 110 captures an image of an object, by means of luminescence light or irradiation light reflected from the object. Here, the luminescence light is emitted from a luminescence substance by means of excitation light. The image capturing section 110 may include a two-dimensional image capturing device such as a CCD and an optical system, where the optical system includes a lens 112. When the light emitted from a luminescence substance is infrared light, the image capturing section 110 is able to capture an infrared light image. When the irradiation light to the object is white light that contains each of RGB components, for example, the image capturing section 110 can capture a visible light image. In this way, the image capturing section 110 can capture an image of an object by means of light emitted from the light irradiation section 150 and reflected from the object.

Note that examples of the light from the object include luminescence light such as fluorescence or phosphor emitted from the luminescence substance existing inside the object, light reflected from the object, or light transmitted through the object. In other words, the image capturing section 110 captures an image of an object, by means of the light emitted from the luminescence substance existing inside the object, the light reflected from the object, or the light transmitted through the object.

Note that the image capturing section 110 can also capture an image of an object in various other methods than a method of utilizing the light from the object. For example, the image capturing section 110 may utilize electromagnetic radiation such as X rays, γ rays, or radial rays that include corpuscular rays such as alpha rays. In addition, the image capturing section 110 may capture an image of an object by utilizing electromagnetic waves, electric waves, or sound waves of various wavelengths.

A clamp 135 is inserted into the clamp port 130, and the clamp port 130 guides the clamp 135 towards the tip 102. Note that the form of the tip of the clamp 135 may be varied. Various types of treatment equipment may be inserted into the clamp port 130 other than a clamp, for the purpose of treating a living organism. The nozzle 138 sends out water or air.

The image capturing section 110 captures images of an object by means of light emitted from the outlets 124a-c respectively. The image processing section 140 processes each image obtained from the image capturing section 110. During this processing, the image processing section 140 calculates the position of the object based on the difference in contrast between each image obtained from the image capturing section 110. Then, the image processing section 140 corrects the blurring occurred in the image of the object according to the position of the object, and supplies the image after correction to the output section 180.

The output section 180 outputs image data having been processed by the image processing section 140. Note that the image capturing control section 160 controls image capturing of the image capturing section 110. The light emission control section 170 controls the light irradiation section 150, by being controlled by the image capturing control section 160. For example, when the image capturing section 110 captures the image of infrared light and irradiation light in a time divisional manner, the light emission control section 170 performs control so that the timing of emitting the infrared light and the irradiation light is synchronized with the image capturing timing of the image capturing section 110.

Figure 2:
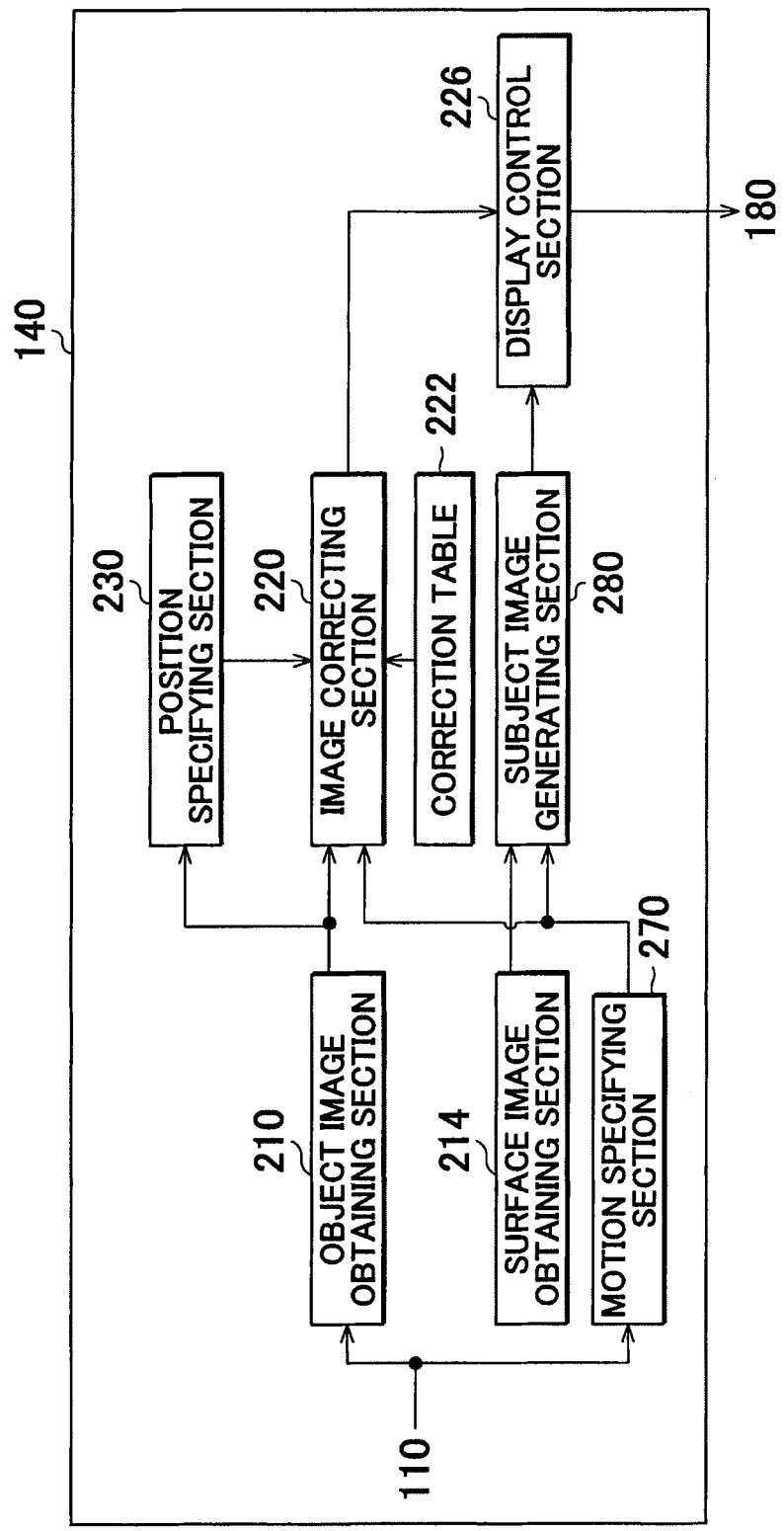
FIG. 2 shows an exemplary configuration of an image processing section 140.

FIG. 2 shows an exemplary configuration of an image processing section 140. The image processing section 140 includes an object image obtaining section 210, a surface image obtaining section 214, an image correcting section 220, a correction table 222, a motion specifying section 270, a subject image generating section 280, a display control section 226, and a position specifying section 230.

The object image obtaining section 210 obtains an image of an object which is an image of light from an object such as a blood vessel existing inside the analyte 20. To be more specific, the object image obtaining section 210 obtains an image captured by the image capturing section 110 by means of the light from the object. Note that the image capturing section 110 captures images of an object existing inside the physical body, by means of rays of light irradiated on different positions. Then, the object image obtaining section 210 obtains each image captured by the image capturing section 110.

When luminescence light emitted from a luminescence substance is used as light from an object, the image of the object obtained by the object image obtaining section 210 includes an object existing in a range of depth from the surface of the physical body in which the excitation light for exciting the luminescence substance can enter. The excitation light of the luminescence substance irradiated from the tip 102 of the endoscope 100 has a wavelength of 750 nm for example, and so reaches a relatively deep portion of the analyte 20 (e.g., about some cm deep).

Therefore, the image of the object obtained by the object image obtaining section 210 includes a blood vessel image existing in a relatively deep portion of the analyte 20. The blood vessel image may be an example of an image of an object. Note that the luminescence substance existing in a range of depth in which the excitation light can reach is excited by the excitation light. Therefore, the image of the object obtained by the object image obtaining section 210 includes a blood vessel image existing in a range of depth in which excitation light can reach.

The position specifying section 230 specifies a depth from a surface of a physical body in which an object exists and which is irradiated with light from the light irradiation section 150, based on the difference in the images of the object captured by the image capturing section 110. Specifically, the position specifying section 230 specifies the depth based on the difference in amount of blurring of the images of the object captured by means of rays of light irradiated at different positions. For example, the position specifying section 230 can specify a larger depth when the difference in the amount of blurring of the images of the object captured by the rays of light irradiated at different positions is smaller.

Note that the position specifying section 230 may specify the depth based on the difference in luminance value between images of the object captured by the rays of light irradiated onto different positions. For example, the position specifying section 230 can specify a larger depth when the difference in the luminance value between the images of the object captured by the rays of light irradiated at different positions is smaller.

Note that the image of the object includes blurring due to dispersion of a physical body from the object to the surface. The image correcting section 220 corrects the blurring of the image of the object based on the depth from the object to the surface specified by the position specifying section 230. To be specific, the image correcting section 220 corrects the spread in the image of the object, based on the depth specified by the position specifying section 230. To be more specific, the image correcting section 220 corrects the spread of the image of the object, based on the depth specified by the position specifying section 230. To be more specific, the image correcting section 220 corrects the spread of the image of the object due to dispersion of the light from the object from the object to the surface of the physical body.

Specifically, the correction table 222 stores a correction value for correcting the spread of the image of the object, in association with the depth of the object. Then, the image correcting section 220 corrects the spread of the object in the image of the object, based on the depth of the object specified by the position specifying section 230 as well as the correction value stored in the correction table 222.

The display control section 226 controls the display of the image of the object after correction by the image correcting section 220, depending on the depth specified by the position specifying section 230. For example, the display control section 226 changes the brightness or the color of each image of the object after correction by the image correcting section 220, according to the depth specified by the position specifying section 230. The image after correction by the image correcting section 220 is supplied to the output section 180 for being displayed.

The surface image obtaining section 214 obtains a surface image that is an image of a surface of a physical body. In other words, the surface image obtaining section 214 obtains an image as it is seen by human eyes. For example, the surface image obtaining section 214 obtains, as a surface image, an image captured by the image capturing section 110 by means of the irradiation light and reflected from a physical body surface. The display control section 226 may display a combination of the image after correction by the image correcting section 220 and the surface image.

Figure 6:
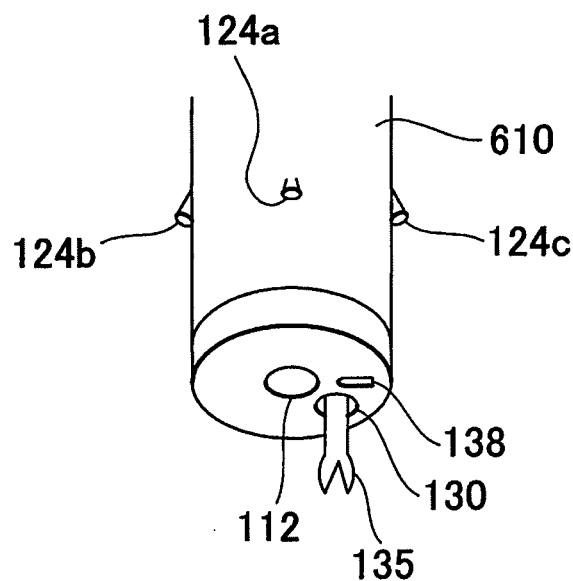
FIG. 6 shows a further different exemplary configuration of the tip 102 of the endoscope 100.

Note that the image capturing section 110 may capture the object image and the surface image at different timings from each other. For example, the image capturing section 110 may successively capture a surface image of visible light by irradiating white light, and capture the object image by emitting excitation light instead of white light at a predetermined timing. In this case, the motion specifying section 270 specifies the motion of the object between the timing at which the excitation light is irradiated and the timing at which the white light is irradiated. The subject image generating section 280 generates a surface image obtained at the timing at which the excitation light is irradiated, based on the surface image obtained by irradiating the white light and the motion specified by the motion specifying section 270. The drawings after FIG. 6 are used to detail the function and operation of the control section 105, the image capturing section 110, the light irradiation section 150, the motion specifying section 270, and the subject image generating section 280, when capturing the object image and the surface image in a time divisional manner.

Note that the position specifying section 220 may specify the depth from the surface down to each of a plurality of objects. The image correcting section 220 may correct the spread of the image of each object, based on the corresponding depth of the object.

The display control section 226 may control the display of the image after correction by the image correcting section 220, according to the depth of each object. For example, the display control section 226 may change the brightness or the color of each object in the image after correction by the image correcting section 220, according to the depth of the object. Additionally, the display control section 226 may display the characters or the like representing the depth of the object, in association with the image after correction.

FIG. 3 shows an exemplary object image captured by an image capturing section 110. An image 300a represents an image captured by the image capturing section 110 by means of light emitted from the outlet 124a. The light from the outlet 124a irradiates a range 350a on the image.

An image 300b represents an image captured by the image capturing section 110 by means of light emitted from the outlet 124b. The light from the outlet 124b irradiates a range 350b on the image. An image 300c represents an image captured by the image capturing section 110 by means of light emitted from the outlet 124c. The light from the outlet 124c irradiates a range 350c on the image.

The image 300a includes a blood vessel image 310a and a blood vessel image 320a. The image 300b includes a blood vessel image 310b and a blood vessel image 320b. The image 300c includes a blood vessel image 310c and a blood vessel image 320c. Note that the blood vessel images 310a-c represent the image of the same blood vessel, and the blood vessel images 320a-c represent the image of the same blood vessel that is different from the blood vessel of the blood vessel images 310a-c.

The position specifying section 230 calculates a luminance value and a contrast value for each of a plurality of regions in the blood vessel images 310a-c. As shown in the drawing, in the image 300a, the maximum luminance value and the maximum contrast value are calculated in the region of the range 350a. In the image 300b, the maximum luminance value and the maximum contrast value are calculated in the region of the range 350b. In the image 300c, the maximum luminance value and the maximum contrast value are calculated in the region of the range 350c. On the other hand, in the region outside the ranges 350a-c, a tremendously low luminance value and a tremendously low contrast value are obtained compared to the ranges 350a-c.

The position specifying section 230 calculates the luminance value and the contrast value for each of the plurality of regions in each of the blood vessel images 320a-c. As shown in this drawing, in the image 300a, the position specifying section 230 calculates the maximum luminance value and the maximum contrast value in the range 350a. However, compared to the blood vessel image 310a, the difference is small between the luminance value and the contrast value in the region other than the range 350a and the luminance value and the contrast value within the range 350a. Also in the image 300b and the image 300c, the difference is small between the luminance value and the contrast value within the range 350b and the range 350c and the luminance value and the contrast value outside the range 350b and the range 350c.

When the difference in the luminance value or the contrast value in the captured blood vessel image is small when the light irradiation section 150 irradiates different positions to perform image capturing, the blood vessel is expected to exist in a deeper position, in the image 300a. Accordingly, the blood vessel captured in the blood vessel images 320a-c is expected to exist in a position deeper than the position of the blood vessel captured in the blood vessel images 310a-c. Utilizing such a difference, the position specifying section 230 calculates the depth in the image capturing direction by the image capturing section 110, from the surface to the blood vessel captured by the image capturing section 110, based on the difference in the luminance value or the contrast value of the blood vessel image when the light irradiation section 150 irradiate different positions to perform image capturing.

As an example, the position specifying section 230 calculates the ratio of the contrast value within the range 350a (e.g., the average value of the contrast value within the range 350a) with respect to the contrast value outside the range 350a (e.g., the average value of the contrast value outside the range 350a). Then, as the ratio gets larger, the position specifying section 230 calculates a position shallower from the surface as the position of the blood vessel shown in the blood vessel images 310a-c.

Moreover, the position specifying section 230 calculates the ratio of the contrast value within the range 350b in the image 300b (e.g., the average value of the contrast value in the range 350b in the image 300b) with respect to the contrast value in the region corresponding to the range 350b in the image 300a (e.g., the average value of the contrast value in the region). The position specifying section 230 may calculate a position shallower from the surface, as the position of the blood vessel shown in the blood vessel images 310a-c, as the ratio gets larger.

Note that the position specifying section 230 may memorize the depth associated with the ratio in advance. The position specifying section 230 may calculate the depth from the surface to the blood vessel based on the depth memorized in association with the ratio memorized in advance.

Figure 4:
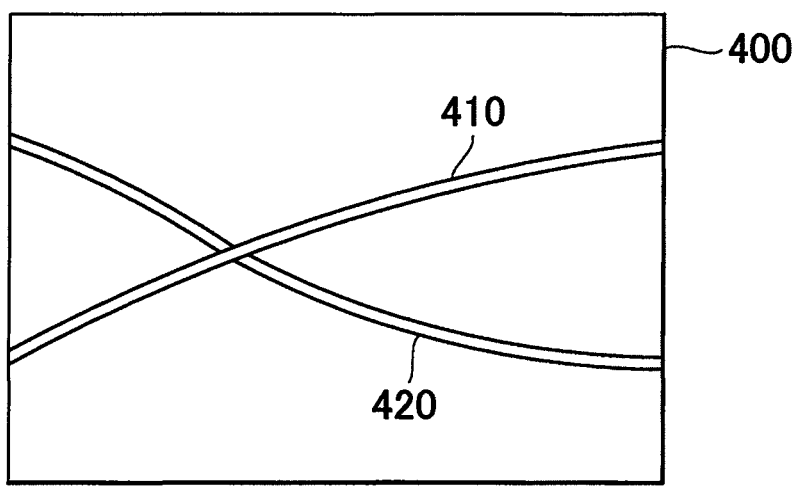
FIG. 4 shows an example of an image 400 after correction by an image correcting section 220.

FIG. 4 shows an example of an image 400 after correction by an image correcting section 220. The image correcting section 220 performs correction to reduce the spread of each blood vessel image according to the depth of the blood vessel calculated by the position specifying section 230 with respect to each blood vessel image included in the image obtained by the object image obtaining section 210.

As an example, the image correcting section 220 obtains a blood vessel image 410 by performing image conversion to reduce the spread in the image of the blood vessel shown in the blood vessel images 310a-c. Specifically, the image correcting section 220 memorizes a point spread function that has the depth of a blood vessel as a parameter. The point spread function shows a point spread caused by dispersion of light from a point light source to the surface. The image correcting section 200 performs filtering on the image of the blood vessel in the blood vessel images 310a-c, where the filtering is performed by means of reverse filtering of a point spread function defined according to the depth of the blood vessel. As a result of the filtering, a blood vessel image 410 is obtained in which the spread of the blood vessel is corrected.

Note that the correction table 222 may memorize the reverse filter that is an example of the correction value, in association with the depth of the object. In the similar manner, the blood vessel image 420 can be obtained with respect to the blood vessel shown by the blood vessel images 320a-c.

The blood vessel image 410 and blood vessel image 420 obtained by using the position specifying system 10 of the present embodiment are clear. Note that the display control section 226 changes the density or the color of the blood vessel image 410 and the blood vessel image 420 according to the depth, to cause the output section 180 to display the depth. Note that the display control section 226 may combine the image after correction by the image correcting section 220 and the surface image obtained by the surface image obtaining section 214, and controls the output section 180 to display the combined image. Specifically, the display control section 226 may overlap the image after correction by the image correcting section 220 and the surface image, and cause the output section 180 to display the overlapped images.

According to the position specifying system 10 of the present embodiment, when for example a doctor performs surgery while viewing the displayed contents on the output section 180, the blood vessel images 410 and 420 which show internal blood vessels invisible through surface observation may sometimes be clearly recognized. In addition, there is an advantage that a doctor can refer to the depth information of the internal blood vessel in the blood vessel images 410 and 420 in surgery or the like.

Figure 5:
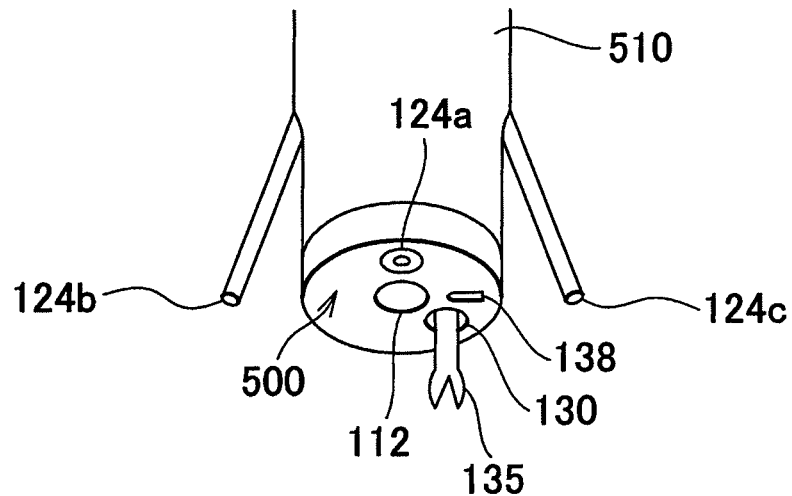
FIG. 5 shows another exemplary configuration of a tip 102 of an endoscope 100.

FIG. 5 shows another exemplary configuration of a tip 102 of an endoscope 100. The configuration in FIG. 5 may be the same as the configuration of the endoscope 100 shown in FIG.

1, except that the outlet 124b and the outlet 124c protrude from the side part 510 of the endoscope 100. Note that the outlet 124b and the outlet 124c are locate in positions different from the end surface 500 of the endoscope 100 provided with the lens 112 and the clamp port 130.

Note that the outlet 124b and the outlet 124c may be located on the same plane on which the outlet 124a is located. The light irradiation section 150 may emit light from the outlets 124a-c while the outlets 124a-c are in contact with the physical body.

FIG. 6 shows a further different exemplary configuration of the tip 102 of the endoscope 100. The outlets 124a-c may be the same as those of the endoscope 100 shown in FIG. 1, except that the outlets 124a-c are provided on the side surface 610 of the endoscope 100.

Figure 7:
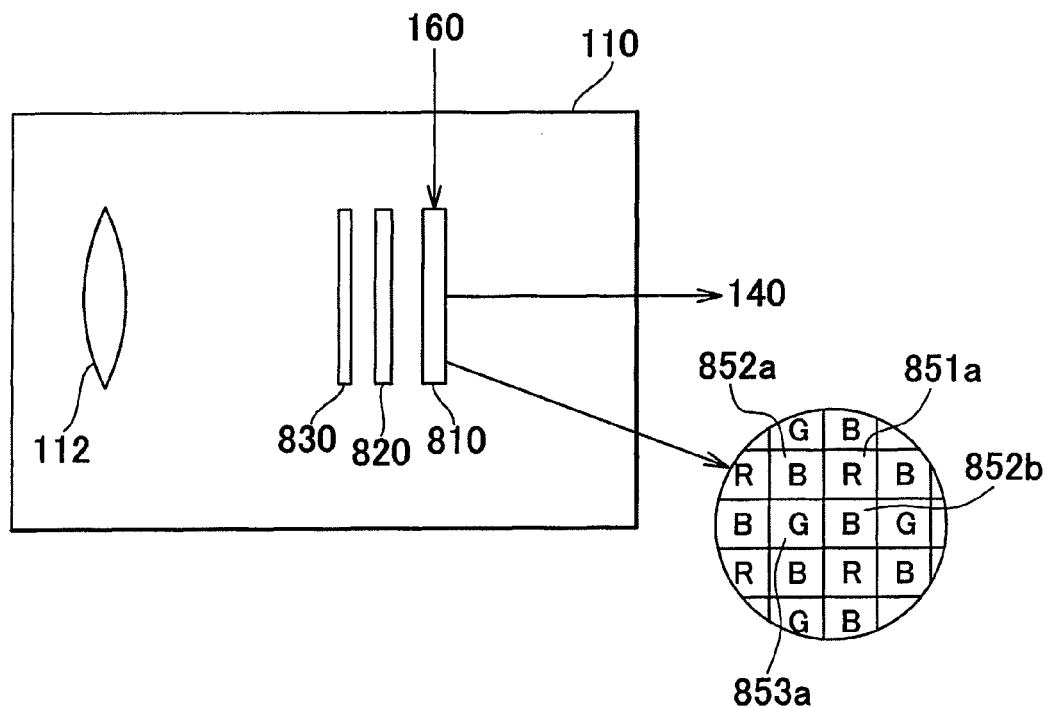
FIG. 7 shows an exemplary configuration of the image capturing section 110.

FIG. 7 shows an exemplary configuration of the image capturing section 110. The image capturing section 110 includes an objective lens 112, an image capturing device 810, a spectral filter 820, and a light-reception excitation light cutting filter 830. The image capturing device 810 includes a plurality of first light receiving elements 851 that include a first light receiving element 851a, a plurality of second light receiving elements 852 that include a second light receiving element 852b, and a plurality of third light receiving elements 853 that include a third light receiving element 853a.

The following explains the function and operation of the constituting elements included in the image capturing sections 110. So as to prevent a complicated explanation, the plurality of first light receiving elements 851 are occasionally collectively referred to as a first light receiving element 851. In the similar manner, the plurality of second light receiving elements 852 are occasionally collectively referred to as a second light receiving element 852, and the plurality of third light receiving elements 853 are occasionally collectively and simply referred to as a third light receiving element 853. Moreover, the plurality of first light receiving elements 851, the plurality of second light receiving elements 852, and the plurality of third light receiving elements 853 are occasionally collectively and simply referred as a light receiving element.

The first light receiving element 851, the second light receiving element 852, and the third light receiving element 853 receive light from a subject supplied via the objective lens 112. Specifically, the first light receiving element 851 receives light of a specific wavelength region as well as light of a first wavelength region that is different from the specific wavelength region. An example of the specific wavelength region is an infrared region such as a wavelength region of luminescence light. The second light receiving element 852 receives light of a second wavelength region that is different from the specific wavelength region. The third light receiving element 853 receives light of a third wavelength region that is different from the specific wavelength region, the first wavelength region, and the second wavelength region.

Note that the first wavelength region, the second wavelength region, and the third wavelength region are different from each other, and include a wavelength region that the other wavelength regions do not include. Note that the first light receiving element 851, the second light receiving element 852, and the third light receiving element 853 are arranged two dimensionally in a predetermined pattern.

The spectral filter 820 includes a plurality of filter elements that transmit any of light of the first wavelength region, light of the second wavelength region, and light of the third wavelength region. Each filter element is arranged two dimensionally to correspond to each light receiving element from among the first light receiving element 851, the second light receiving element 852, and the third light receiving element 853. Each individual light receiving element receives light that has transmitted through the corresponding filter element. In this way, the first light receiving element 851, the second light receiving element 852, and the third light receiving element 853 receive light in a wavelength region different from each other.

The light-reception excitation light cutting filter 830 is provided at least between the subject and the second light receiving element 852 and the third light receiving element 853, and cuts light of a wavelength region of excitation light. The second light receiving element 852 and the third light receiving element 853 receive light reflected from a subject via the light-reception excitation light cutting filter 830. For this reason, the second light receiving element 852 and the third light receiving element 853 do not substantially receive reflection light excitation light after reflection from a physical body.

Note that the light-reception excitation light cutting filter 830 may cut the light of a wavelength region of excitation light and light of the specific wavelength region. In this case, the second light receiving element 852 and the third light receiving element 853 do not substantially receive luminescence light from a subject for example.

Note that the light-reception excitation light cutting filter 830 may be provided between a subject and the first light receiving element 851. In this case, the light-reception excitation light cutting filter 830 provided between the subject and the first light receiving element 851 transmits light of the specific wavelength region.

Note that the light-reception excitation light cutting filter 830 may include filter elements arranged two dimensionally to correspond to each of the first light receiving element 851, the second light receiving element 852, and the third light receiving element 853, just as the spectral filter 820. The filter element that supplies light to the first light receiving element 851 transmits the light of at least the first wavelength region and the specific wavelength region. Note that the filter element that supplies light to the first light receiving element 851 may cut the light of the wavelength region of the excitation light. The filter element that supplies light to the second light receiving element 852 cuts the light of the wavelength region of the excitation light and the light of the specific wavelength region, and transmits at least the light of the second wavelength region. The filter element that supplies light to the third light receiving element 853 cuts the light of the wavelength region of the excitation light and the light of the specific wavelength region, and transmits at least the light of the third wavelength region.

The image processing section 140 determines the pixel value of one pixel based at least on the amount of light received by the first light receiving element 851a, the second light receiving element 852a, the second light receiving element 852b, and the third light receiving element 853a. That is, one pixel element is formed by the two dimensional arrangement of the first light receiving element 851a, the second light receiving element 852a, the second light receiving element 852b, and the third light receiving element 853a. The pixel element arrangement is further arranged two dimensionally to form a plurality of pixel elements. Note that the light receiving elements may also be arranged in arrangements other than the arrangement shown in the present drawing.

Figure 8:
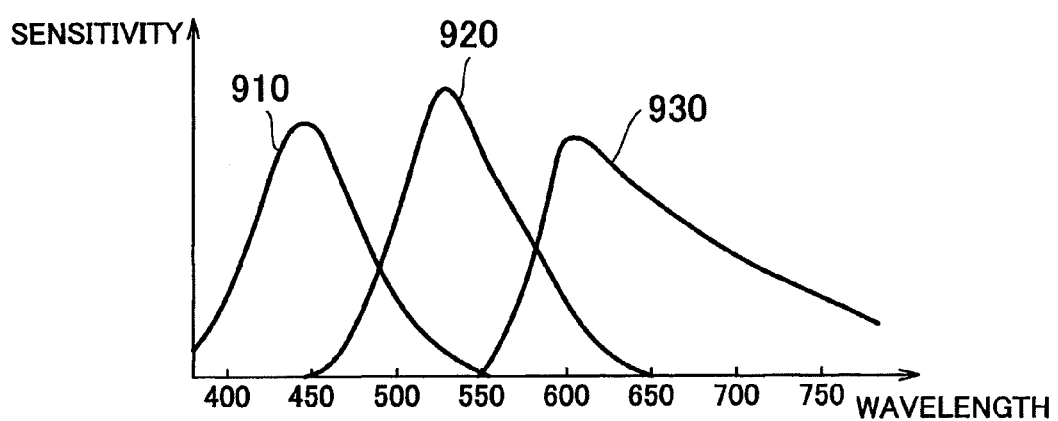
FIG. 8 shows an exemplary spectral sensitivity characteristic of a first light receiving element 851, a second light receiving element 852, and a third light receiving element 853.

FIG. 8 shows an exemplary spectral sensitivity characteristic of a first light receiving element 851, a second light receiving element 852, and a third light receiving element 853. The line 930, the line 910, and the line 920 represent the spectral sensitivity distributions respectively of the first light receiving element 851, the second light receiving element 852, and the third light receiving element 853. For example, the first light receiving element 851 is sensitive to the light of the wavelength near 650 nm to which the other light receiving elements are not substantially sensitive. The second light receiving element 852 is sensitive to the light of the wavelength near 450 nm to which the other light receiving elements are not substantially sensitive. The third light receiving element 853 is sensitive to the light of the wavelength near 550 nm to which the other light receiving elements are not substantially sensitive.

The first light receiving element 851 is able to receive light of a infrared region that is one example of the specific wavelength region (e.g., 810 nm). This spectral sensitivity characteristic is due to the transmittance characteristic of the light-reception excitation light cutting filter 830 and the spectral filter 820 as well as the spectral sensitivity of each light receiving element.

In this way, the first light receiving element 851, the second light receiving element 852, and the third light receiving element 853 receive light of R component, light of B component, and light of G component, respectively. In addition, the first light receiving element 851 can also receive light of the infrared region that is one example of the specific wavelength region. Note that the first light receiving element 851, the second light receiving element 852, and the third light receiving element 853 may be an image capturing device such as CCD and CMOS. The first light receiving element 851, the second light receiving element 852, and the third light receiving element 853 have the spectral sensitivity characteristic shown by the line 930, the line 910, and the line 920, due to the combination of the spectral transmittance of the light-reception excitation light cutting filter 830, the spectral transmittance of the filter elements of the spectral filter 820, and the spectral sensitivity of the image capturing device itself.

Figure 9:
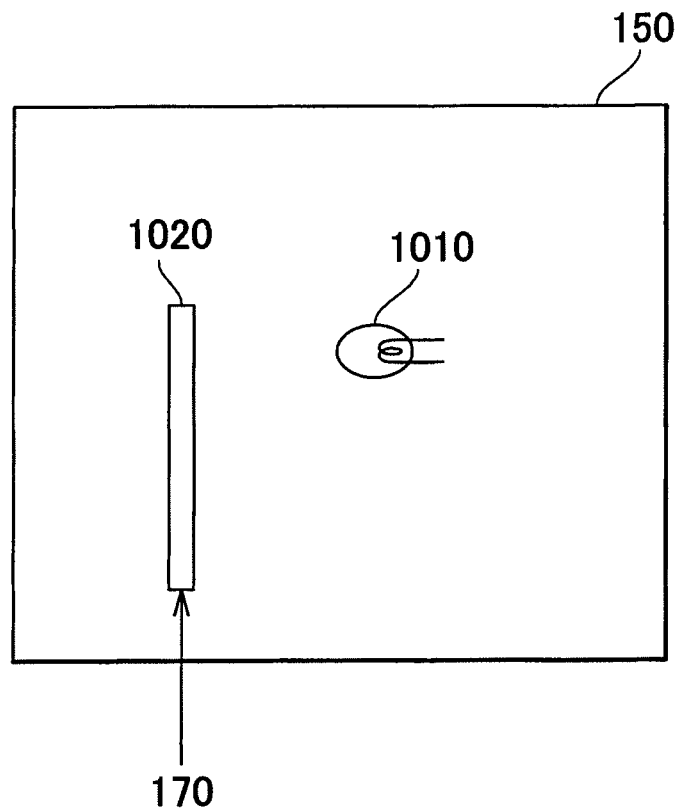
FIG. 9 shows an exemplary configuration of a light irradiation section 150.

FIG. 9 shows an exemplary configuration of a light irradiation section 150. The light irradiation section 150 includes a light emission section 1010 and a light-source filter 1020. The light emission section 1010 emits light of a wavelength region that includes a wavelength region of excitation light, a first wavelength region, a second wavelength region, and a third wavelength region. In the present embodiment, the light emission section 1010 may be a xenon lamp for example.

Figure 10:
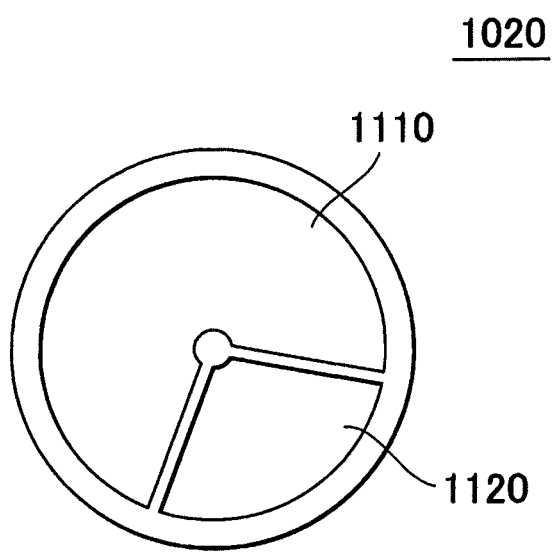
FIG. 10 shows an exemplary configuration of a light-source filter 1020.

FIG. 10 shows an exemplary configuration of a light-source filter 1020. FIG. 10 shows a configuration seen in the direction in which the light is directed from the light emission section 1010 to the light-source filter 1020. The light-source filter 1020 includes an irradiation light cutting filter 1120 and an excitation light cutting filter 1110. Note that the light emission control section 170 rotates the light-source filter 1020 on a plane substantially vertical to the direction in which the light emitted from the light emission section 1010 travels, with the central axis of the light-source filter 1020 being the center.

The excitation light cutting filter 1110 substantially cuts the light of the wavelength region of the excitation light and transmits the light of the first wavelength region, the light of the second wavelength region, and the light of the third wavelength region. In addition, the irradiation light cutting filter 1120 transmits the light of the wavelength region of the excitation light, the light of the second wavelength region, and the light of the third wavelength region. Note that the irradiation light cutting filter 1120 desirably substantially cuts the light of the first wavelength region. Note that the light from the light emission section 1010 is directed to a position out of the central axis of the light-source filter 1020.

Accordingly, at the timing at which the light from the light emission section 1010 is directed to the excitation light cutting filter 1110, from among the light from the light emission section 1010, the light of the wavelength region of the excitation light is substantially cut by the excitation light cutting filter 1110, and the light of the first wavelength region, the light of the second wavelength region, and the light of the third wavelength region are transmitted through the excitation light cutting filter 1110. Consequently, at this timing, the light of the first wavelength region, the light of the second wavelength region, and the light of the third wavelength region are substantially irradiated onto the subject.

At the timing at which the light from the light emission section 1010 is directed to the irradiation light cutting filter 1120, from among the light from the light emission section 1010, the light of the wavelength region of the excitation light, the light of the second wavelength region, and the light of the third wavelength region are transmitted through the irradiation light cutting filter 1120. At this timing, the excitation light, the light of the second wavelength region, and the light of the third wavelength region are substantially irradiated onto the subject.

By being controlled by the image capturing control section 160, at the timing at which the light of the first wavelength region, the light of the second wavelength region, and the light of the third wavelength region, which are visible light, are irradiated, the image capturing section 110 receives the reflection light resulting from reflection of the irradiation light from the analyte 20. The surface image obtaining section 214 generates a subject image by means of the visible light as one example of a surface image, based on the amount of light received by the image capturing section 110. When the irradiated light is substantially white light, the surface image can be said to be a white light image.

In addition, by being controlled by the image capturing control section 160, at the timing at which the excitation light, the light of the second wavelength region, and the light of the third wavelength region are irradiated, the image capturing section 110 receives luminescence light emitted from ICG within the subject, and reflection light resulting from reflection, from the analyte 20, of the light of the second wavelength region and the light of the third wavelength region. The object image obtaining section 210 obtains, from the first light receiving element 851, a signal according to the amount of light received by the first light receiving element 851, and generates a subject image of luminescence light, based on the amount of luminescence light received by the first light receiving element 851. The surface image obtaining section 214 generates a subject image of visible light, based on the amount of the light of the second wavelength region and the light of the third wavelength region based on a signal from the second light receiving element 852 and the third light receiving element 853, and the amount of the light of the first wavelength region received by the first light receiving element 851 at the other timing.

Figure 11:
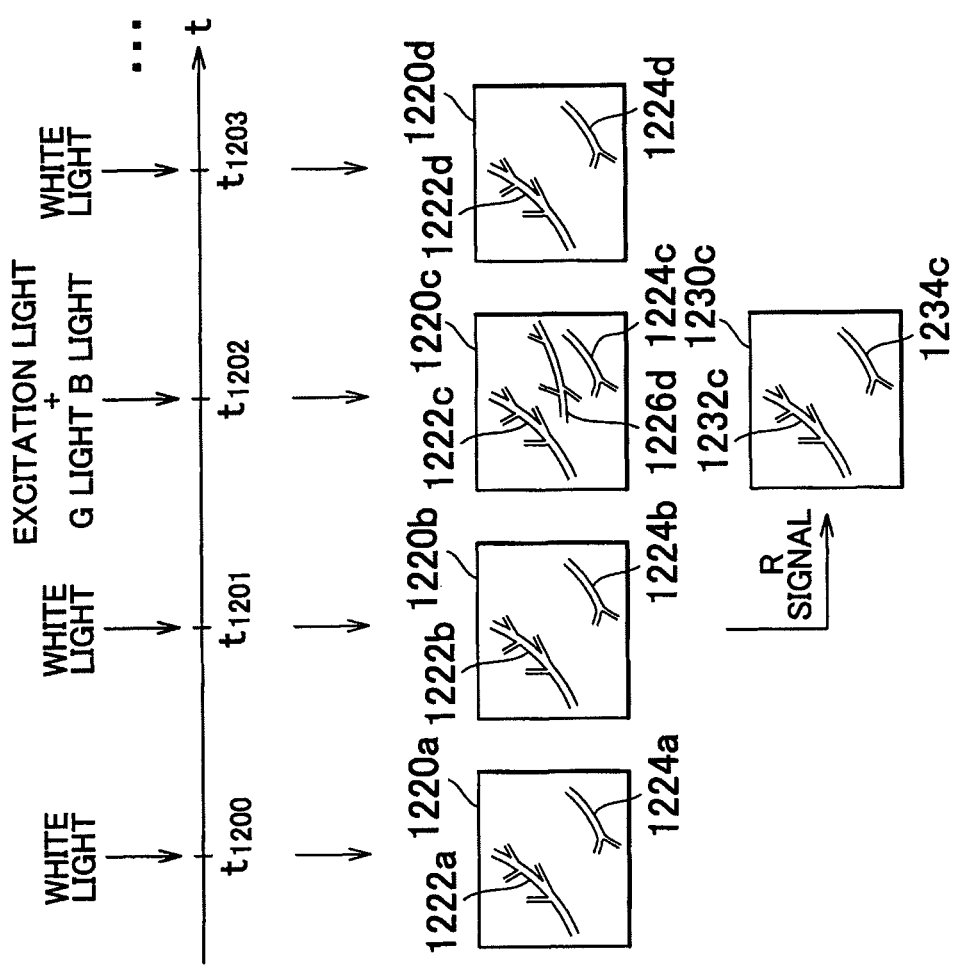
FIG. 11 shows an example of an image capturing timing by the image capturing section 110 as well as a image generated by the image processing section 140.

FIG. 11 shows an example of an image capturing timing by the image capturing section 110 as well as a image generated by the image processing section 140. The image capturing control section 160 causes the image capturing section 110 to capture an image by means of the light from the object, at the times t1200, t1201, t1202, t1203, . . . etc. By the timing control by the image capturing control section 160, the light emission control section 170 irradiates the subject with the light emitted from the light emission section 1010 through the excitation light cutting filter 1110, at the first timing that includes the times t1200, t1201, and t1203. In this way, by being controlled by the light emission control section 170, the light irradiation section 150 irradiates the subject with the light of the wavelength region that includes the first wavelength region, the second wavelength region, and the third wavelength region, at the first timing.

At the first timing, the image capturing control section 160 causes the first light receiving element 851 to receive the light of the first wavelength region, from among the reflection light resulting from reflection, from the subject, of the light of the wavelength region that includes the first wavelength region, the second wavelength region, and the third wavelength region. Moreover, from among the reflection light, the image capturing control section 160 causes the second light receiving element 852 to receive the light of the second wavelength region, and from among the reflection light, the image capturing control section 160 causes the third light receiving element 853 to receive the light of the third wavelength region. In this way, at the first timing, the image capturing control section 160 causes the first light receiving element 851 to receive the light of the first wavelength region from the subject, the second light receiving element 852 to receive the light of the second wavelength region from the subject, and the third light receiving element 853 to receive the light of the third wavelength region from the subject.

At the second timing that includes the time t1202, the light emission control section 170 irradiates the subject with the light emitted by the light emission section 1010 through the irradiation light cutting filter 1120, according to the timing control by the image capturing control section 160. In this way, according to the control by the light emission control section 170, the light irradiation section 150 irradiates the subject with the light of the wavelength region that includes the excitation light, the second wavelength region, and the third wavelength region, at the second timing.

At the second timing, the image capturing control section 160 causes the first light receiving element 851 to receive the light of the specific wavelength region emitted from the subject. That is, at the second timing, the image capturing control section 160 causes the first light receiving element 851 to receive the light of the specific wavelength region from the subject.

In this way, at the second timing, the control section 105 irradiates the subject with the excitation light, the light of the second wavelength region, and the light of the third wavelength region, without irradiating the subject with the light of the first wavelength region. As a result, the control section 105 causes the first light receiving element 851 to receive the light of the specific wavelength region emitted from the subject, causes the second light emitting element 852 to receive the light of the second wavelength region from among the reflection light reflected from the subject, and causes the third light receiving element 853 to receive the light of the third wavelength region from among the reflection light. Note that the wavelength region of the excitation light is different from any of the first wavelength region, the second wavelength region, or the third wavelength region, and includes a wavelength region that is not included in any of the first wavelength region, the second wavelength region, and the third wavelength region.

As explained so far, the control section 105 controls the spectrum of light to be received by the first light receiving element 851, the second light receiving element 852, and the third light receiving element 853. The image processing section 140 generates an image by means of the light of each wavelength region based on the amount of the light received by the light receiving element at each timing.

Specifically, the surface image obtaining section 214 generates a subject image 1220a, a subject image 1220b, and a subject image 1220d, based on the amount of light received by the light receiving element at a timing represented by each of the times t1200, t1201, and t1203. The subject image 1220a, the subject image 1220b, and the subject image 1220d are substantially recognized as a visible light image obtained when white light is irradiated. The subject image 1220a includes a blood vessel image 1222a and a blood vessel image 1224a, and the subject image 1220b includes a blood vessel image 1222b and a blood vessel image 1224b, and the subject image 1220d includes a blood vessel image 1222d and a blood vessel image 1224d.

Note that the subject image 1220a, the subject image 1220b, and the subject image 1220d include a surface image that is an image of a surface of a physical body, other than a blood vessel image. In this way, the surface image obtaining section 214 generates a surface image of a subject at the first timing, by means of the light of the first wavelength region received by the first light receiving element 851 at the first timing, the light of the second wavelength region received by the second light receiving element 852 at the first timing, and the light of the third wavelength region received by the third light receiving element 853 at the first timing.

In addition, the object image obtaining section 210 generates a subject image 1220c that includes a blood vessel image 1222c, a blood vessel image 1224c, and a blood vessel image 1226c, based on the amount of light received by the light receiving element at the timing represented by the time t1202. The subject image 1220c can be recognized as an image of a subject by means of the luminescence light form the subject. Note that the subject image 1220c is an image to go through the blur correction processing by the image correcting section 220, which was described above.

In addition, the subject image generating section 280 generates a subject image 1230c that includes a blood vessel image 1232c and a blood vessel image 1234c, based on the amount of light received by the first light receiving element 851 at the timing represented by the time t1201 and the amount of light received by the second light receiving element 852 and the third light receiving element 853 at the timing represented by the time t1202. The subject image 1230c can be recognized as a subject image by means of visible light, which should be obtained at the timing represented by the time t1202.

In this way, the image processing section 140 generates a subject image by means of the light of the first wavelength region received by the first light receiving element 851 at the first timing and the visible light at the second timing, by using the light of the second wavelength region received by the second light receiving element 852 at the second timing. Accordingly, even at the timing at which the luminescence light image is being captured, the image processing section 140 is able to generate an image by means of the visible light. The output section 180 can provide an image without any frame dropping, by consecutive display of the subject image 1220a, the subject image 1220b, the subject image 1230c, the subject image 1220d, . . . .

When the analyte 20 is a living organism (e.g., human body) that contains red blood, the space frequency component of R component in the visible light image is usually smaller than the space frequency components of G component and B component. For this reason, the degree of deterioration of the image from which R component frames are dropped is smaller than the degree of deterioration of the image from which frames of G component or B component are dropped. For this reason, the image from which R component frames are dropped looks natural to the human eyes that are observing the image, compared to the image from which frames of G component or B component are dropped. Therefore, the position specifying system 10 can provide a visible light image substantially without frame dropping as image contents.

As described above, the position specifying system 10 can capture the subject image 1220c, by the luminescence light of the infrared region caused from the analyte 20 due to the excitation light of the infrared region. The excitation light having a longer wavelength than the visible light is hard to be observed by a physical body compared to the visible light. Therefore, the excitation light tends to cause luminescence light in the analyte 20 by entering deep (e.g., about 1 cm deep) in the physical body, in comparison with the visible light. In addition, the luminescence light has a wavelength further longer than the excitation light, and so is easier to reach the surface of the physical body. For this reason, the position specifying system 10 can obtain a subject image 1220c that contains a blood vessel image 1226d in a deeper layer, which is not contained in the subject image 1220a, the subject image 1220b, or the subject image 1220d obtained by the visible light.

The output section 180 may generate a combined image by combining the subject image 1220c with the subject image 1220b or with the subject image 1220d captured at the timing in the vicinity of the timing at which the subject image 1220c is captured, and outputs the combined image to outside. For example, the output section 180 may display the combined image. In addition, the output section 180 may record the subject image 1220c in association with the subject image 1220b or with the subject image 1220d.

At the timing at which the visible light image is captured, the control section 105 irradiates the subject with the light from the light emission section 1010, by cutting the light of the wavelength region of the excitation light and the wavelength region of the luminescence light. For this reason, the position specifying system 10 is able to provide an image of a surface of a physical body suitable for observation, which is a visible light image that does not include a blood vessel image inside a physical body.

Figure 12:
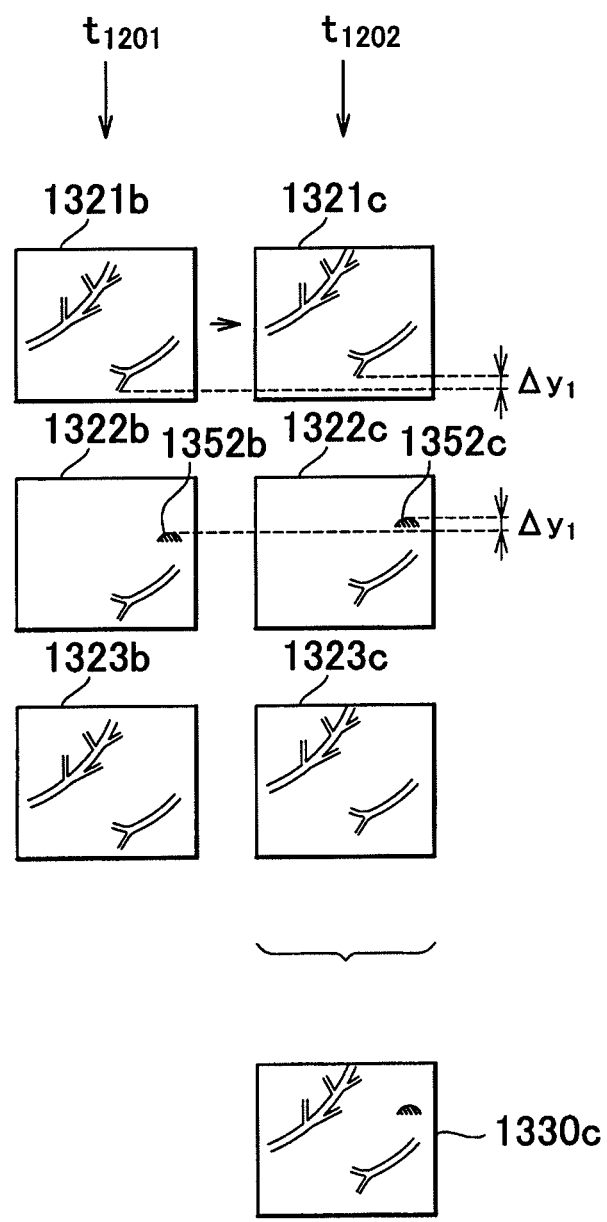
FIG. 12 explains generation of a surface image in which the motion has been corrected.

FIG. 12 explains generation of a surface image in which the motion has been corrected. In FIG. 11, so as to facilitate the explanation, the motion of the tip 102 of the endoscope 100, the motion of the analyte 20, or the like are assumed not to cause a temporal change of the image, and an example of processing for generating the subject image 1230c by multiplexing the R signal corresponding to the amount of light received by the first light receiving element 851 at the timing of the time t1201 and the B signal and the G signal respectively corresponding to the amount of light received by the second light receiving element 852 and the third light receiving element 853 at the timing t1202. This processing may cause a difference between the R signal and the signals of the other colors in the visible light image, due to the motion of the tip 102 of the endoscope 100 or the motion of the analyte 20.

Figure 13:
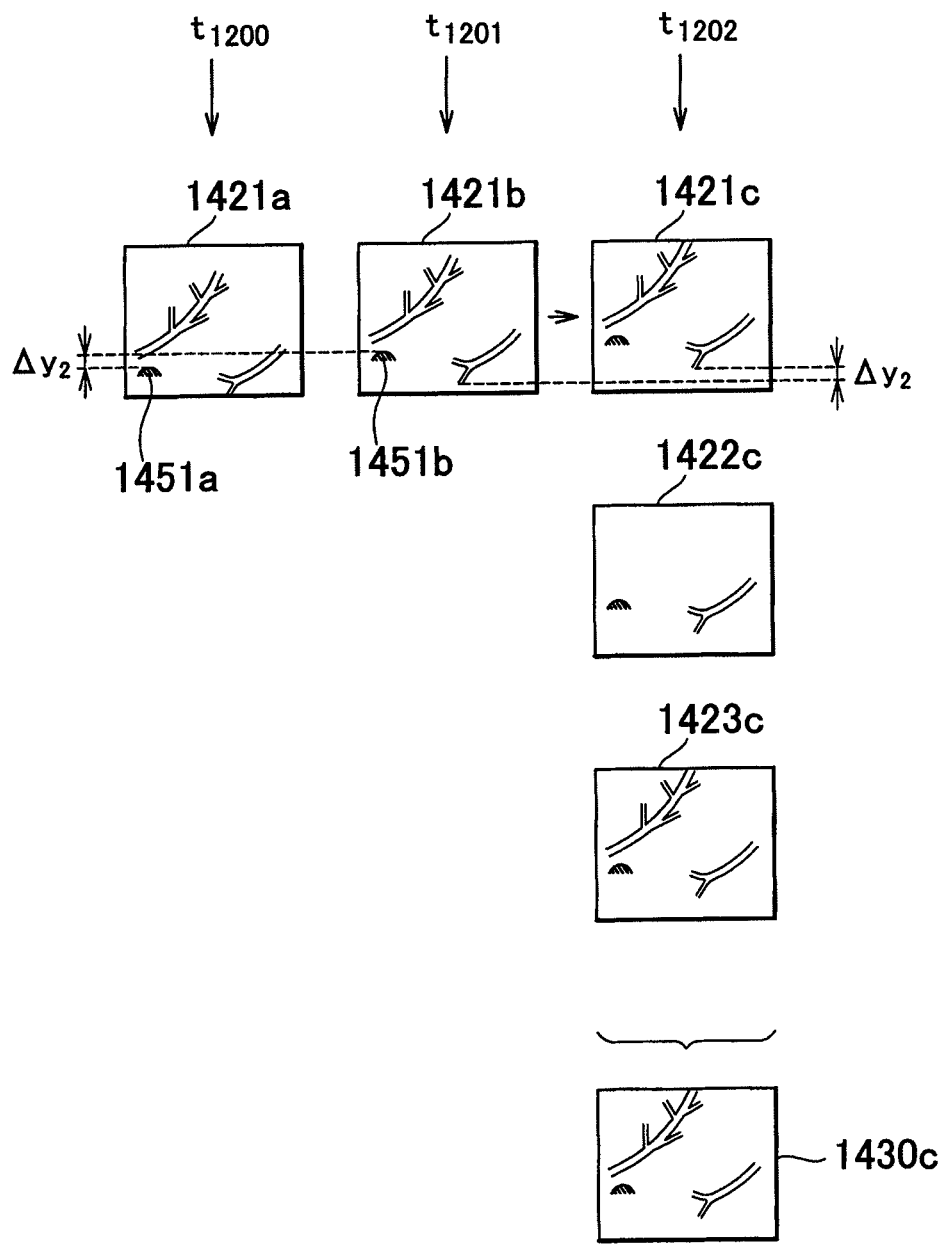
FIG. 13 explains another example of generation of the surface image in which the motion has been corrected.

In relation to FIGS. 12 and 13, the operation and function of the image processing section 140 for correcting the effect of the visible light image due to the motion are explained. Especially, the operation of the motion specifying section 270 and the subject image generating section 280 is extensively explained.

The motion specifying section 270 specifies the motion of the object in the image, based on the image of the B signal at a plurality of timings. Here, the motion of the object includes a motion that causes the temporal change of the image such as a motion of the analyte 20 itself, a motion of the tip 102 of the endoscope 100, and a temporal change of the zoom value of the image capturing section 110. In addition, the motion of the tip 102 of the endoscope 100 includes the temporal change of the position of the tip 102 that causes the temporal change of the image capturing position of the image capturing section 110 and the temporal change in the direction of the tip 102 that causes the temporal change of the image capturing position of the image capturing section 110.

Here, the motion specifying section 270 specifies the motion of the object, based on the image of the B signal, at the time t1201 and the time t1202. For example, the motion specifying section 270 may specify the motion of the object, by matching the objects respectively extracted from the plurality of images.

The subject image generating section 280 corrects the R signal at the timing of the time t1201 based on the motion, and generates the R signal that should be obtained at the timing of the time t1202. Then, the subject image generating section 280 generates the surface image at the time t1202, by multiplexing the R signal generated by the correction, the B signal at the timing of the time 1202, the G signal at the timing of the time t1202.

The image 1321b is an image of the R signal from the first light receiving element 851 at the time t1201. The image 1322b and the image 1322c are respectively an image of the B signal from the second light receiving element 852 at the time t1201 and the time t1202. The image 1323b and the image 1323c are respectively an image of the G signal from the third light receiving element 853 at the time t1201 and the time t1202.

Here, the motion specifying section 270 specifies the motion based on the image contents of the image 1322b and the image 1322c. Specifically, the motion specifying section 270 extracts an object representing the same subject, from the image 1322b and the image 1322c. In the example of the present drawing, the object 1352b and the object 1352c are extracted from the image 1322b and the image 1322c.

The motion specifying section 270 calculates the difference in position between the object 1352b and the object 1352c. In the example of the present drawing, to facilitate the explanation, the difference in the position is assumed to be caused in the y direction on the image. In this example, the motion specifying section 270 calculates the positional difference $\Delta y1$ between the position of the object 1352b and the position of the object 1352c.

The subject image generating section 280 shifts the image 1321b in the y direction by the amount corresponding to the calculated positional difference $\Delta y1$ thereby generating the image 1321c. The subject image generating section 280 combines the image 1321c, the image 1322c, and the image 1323c, to generate the surface image 1330c. Note that in this case, the combining processing includes processing to multiplex the R signal representing the image 1321c, the B signal representing the image 1322c, and the G signal representing the image 1323c at a predetermined weight.

The case of specifying the motion using the image 1322 of the B signal is explained in the above. In other cases, it is possible to specify the motion using the image 1323 of the G signal. Which image of wavelength region is used for specifying the motion of the motion specifying section 270 may be determined based on the contrast of the captured image. For example, the motion specifying section 270 may specify the motion by using the images in which the contrast is larger. When the image of the minute structure can be used as an object for specifying a motion (e.g., the image of the minute structure on the surface is clear), the image of the B signal may be used to more accurately specify the motion. When the image of the concave/convex structure can be used as an object for specifying a motion (e.g., the image of the concave/ convex structure is clear on the surface), the image of the G signal may be used to more accurately specify the motion.

In addition, the subject image generating section 280 may differ the amount of correction of the motion with respect to the image of the R signal for each image region. For example, when the image capturing direction of the image capturing section 110 is vertical to the surface of the subject, and the tip 102 of the endoscope 100 moves horizontal with respect to the surface of the subject, the amount of movement of the object can be considered equal in each image region. On the contrary, when for example the image capturing direction of the image capturing section 110 is not vertical to the surface of the subject, the amount of the motion in the image region in which a region far from the tip 102 is captured can be smaller than the image region in which a region near the tip 102 is captured.

For the subject image generating section 280 to calculate the motion correction amount with respect to the image of the R signal for each image region, if the positional relation between the surface of the subject and the image capturing section 110 is known or can be estimated, the subject image generating section 280 may calculate the motion correction amount based on the positional relation and the position of the image region. Note that the subject image generating section 280 obtains the control value for operating the endoscope 100 that causes the temporal change of the image, such as a control value for controlling the position or the direction of the tip 102 or the control value for controlling the zoom value of the image capturing section 110, to calculate the motion correction amount with respect to the image of the R signal based on the control value.

Alternatively, the motion specifying section 270 may calculate the motion of the object for each image region. The subject image generating section 280 may calculate the motion correction amount with respect to the image of each image region, based on the motion of the object in each image region.

Note that when specifying the motion for each image region, the motion specifying section 270 may determine, for each image region, which image of light of wavelength region should be used to specify the motion in the image region. For example, the motion specifying section 270 calculates the contrast in each image in each image region. In each image region, the motion specifying section 270 may select a plurality of images by light of a wavelength region in which a large contrast has been calculated, over other wavelength images, to specify the motion of the object using the selected plurality of images.

As described in relation to FIGS. 11 and 12, the motion specifying section 270 specifies the motion of the object on the image between the first timing and the second timing, based on the image of the light of the second wavelength region received by the second light receiving element 852 in the first timing and the image of the light of the second wavelength region received by the plurality of second light receiving elements 852 at the second timing. Then, the subject image generating section 280 generates the surface image of the second timing, based on the light of the first wavelength region received by the first light receiving element 851 at the first timing, the light of the second wavelength region received by the second light receiving element 852 at the second timing, and the motion.

FIG. 13 explains another example of generation of the surface image in which the motion has been corrected. In the example of the present drawing, the motion specifying section 270 specifies the motion of the object using the image 1421*a* of the R signal obtained at the timing of the time t1200 and the image 1421*b* of the R signal obtained at the timing of the time t1201. Utilizing the method explained with reference to FIG. 12, the motion specifying section 270 extracts objects representing the same object, from the image 1421*a* and the image 1421*b*. In the example of the present drawing, the motion specifying section 270 extracts the object 1451*a* and the object 1451*b* respectively from the image 1421*a* and the image 1421*b*.

The motion specifying section 270 calculates the difference in position between the object 1451*a* and the object 1451*b*. In the example in the present drawing, too, so as to facilitate the explanation, the positional difference is assumed to be caused in the y direction on the image. In view of this, the motion specifying section 270 calculates the positional difference $\Delta y2$ between the position of the object 1451*a* and the position of the object 1451*b*. Then, utilizing the method explained with reference to FIG. 12, the subject image generating section 280 shifts the image 1421*b* in the y direction by the amount corresponding to the calculated positional difference $\Delta y2$, thereby generating the image 1421*c*. The subject image generating section 280 generates the surface image 1430*c*, by combining the image 1421*c*, the image 1422*c* that is the image of the G signal from the third light receiving element 853 at the time t1202, and the image 1423*c* that is the image of the G signal from the third light receiving element 853 at the time t1202.

Note that the motion is specified utilizing the image 1421*a* and the image 1421*b* in the above explanation, the motion specifying section 270 may specify the motion by using the image 1421*b*, as well as the image of the R signal obtained at the time t1203. In this way, the motion specifying section 270 may specify the motion by the image obtained at a plurality of timings that include the timing of the time before or after the time t1201 that is the time at which the image of the R signal in which the motion has been corrected should be generated. When it is possible to allow the display of the visible light image to be delayed for a certain time, the images of the later timings may be utilized to further enhance the accuracy in specifying the motion.

As explained above with reference to FIG. 13, the motion specifying section 270 specifies the motion of the object on the image among a plurality of timings, based on the plurality of images by means of the light of the first wavelength region received by the first light receiving element 851 at a plurality of timings other than the second timing but includes the first timing. Then, the subject image generating section 280 generates the surface image at the second timing, based on the light of the first wavelength region received by the first light receiving element 851 at the first timing, the light of the second wavelength region received by the second light receiving element 852 at the second timing, and the motion.

As an example of the motion specifying processing, the processing to specify the motion is performed with use of the images captured at two timings by the motion specifying section 270 in FIGS. 12 and 13. However, the motion specifying section 270 may specify the motion with use of the images captured at three or more timings. In addition, the motion specifying section 270 may select an image of wavelength region to be used for specifying the motion, from among the images of the R signals, for each image region, in addition to the image of the B signal and the image of the G signal.

Note that when performing the blur correcting processing described above to the subject image 1220*c*, the object image correcting section 220 may specify which of the blood vessel image 1222 and the blood vessel image 1224 contained in the other subject image 1220, the blood vessel image 1222*c* and the blood vessel image 1224c contained in the subject image 1220c correspond to, based on the motion specified by the motion specifying section 270.

In addition, the second light receiving element 852 and the third light receiving element 853 are sensitive to the light of the wavelength region of the luminescence light, and may receive luminescence light from the subject at the timing represented by the time t1202. In this case, the spectral filter 820 and the light-reception excitation light cutting filter 830 may transmit the light of the wavelength region of the luminescence light.

In this case, the object image obtaining section 210 may generate an object image by performing pixel addition processing for adding image signals from a plurality of neighboring light receiving elements from among the first light receiving element 851, the second light receiving element 852, and the third light receiving element 853. Note that the image signal from the light receiving element may be a signal representing the amount of charge corresponding to the amount of light received by each light receiving element. The signal representing the amount of charge may be an analogue signal corresponding to the amount of light received by each light receiving element, or a digital signal obtained by performing A/D conversion on the analogue signal. The signal component can be increased utilizing any type of pixel addition processing. The amount of increase in random noise component due to the pixel addition processing is smaller than the amount of increase in signal component due to the pixel addition processing. For this reason, the S/N ratio can be improved compared to a case where the pixel addition processing is not performed.

The motion specifying section 270 may specify the motion by utilizing any of the R signal, the G signal, and the B signal obtained at a plurality of timings other than the timing represented by the time t1202, as in the method explained with reference to FIGS. 12 and 13. Then, based on the motion, the subject image generating section 280 can generate a subject image of visible light that should be obtained at the timing represented by the time t1202, by correcting the subject image of the visible light obtained at the timing other than the timing represented by the time t1202.

In the above explanation, as the configuration of the light irradiation section 150, shown is a configuration of utilizing a single light source and a rotation filter capable to emitting light including a wavelength region of visible light and a wavelength region of excitation light. Alternatively, the light irradiation section 150 can emit light including excitation light or visible light in a time divisional manner, by controlling the light emission of a plurality of light emitting elements that emit light of different wavelength regions. For example, the light emitting element that emits light of a visible light region may be a semiconductor device such as LED. Also for example, the light emitting element that emits excitation light may be a semiconductor device such as a semiconductor laser. In addition, a phosphor that emits luminescence light such as fluorescence by being excited may be used as a light emitting element.

Note that the light emission control section 170 may emit light including excitation light or visible light in a time divisional manner, by controlling the light emission intensity of each of a plurality of light emitting elements at each timing. "Controlling the light emission intensity of each of a plurality of light emitting elements at each timing" includes differing the combination of light emitting elements to emit light at each timing.

In addition, a light emitting element may be provided for the tip 102 of the endoscope 100. Note that the light emitting element may emit light by means of electric excitation, or may emit light by optical excitation. When the light emitting element emits light by optical excitation, the light irradiation section 150 may include an excitation section that emits light for exciting the light emitting element, and the light emitting element. Here, the light emitting element may emit light of a different spectrum for each wavelength of light for excitation. In this case, the light emission control section 170 may control the spectrum of irradiation light, by controlling the wavelength of light for excitation emitted from the excitation section, at each timing. The spectrum of light emitted by each light emitting element by means of the same light for excitation may be different for each light emitting element. In addition, from among the light for excitation, the light transmitted through the light emitting element may be irradiated onto the subject as irradiation light.

Note that in the above explanation, the configuration that includes a spectral filter 820 at the light reception side of the image capturing section 110. However, the image capturing section 110 may not include a spectral filter 820. In this case, the light irradiation section 150 may irradiate the light of the R wavelength region, the light of the G wavelength region, the light of the B wavelength region, and the light of the wavelength region of the excitation light in a time divisional manner. By multiplexing the signals from the light receiving elements at the timing at which visible light is irradiated, the surface image obtaining section 214 can generate a subject image of visible light. In addition, the object image obtaining section 210 may generate a subject image of luminescence light by means of a signal from a light receiving element at the timing at which excitation light is irradiated.

Note that the configuration of the light irradiation section 150 for irradiating the light of the R wavelength region, the light of the G wavelength region, the light of the B wavelength region, and the light of the wavelength region of the excitation light in a time divisional manner may include one or more light sources for emitting light of a wavelength region that includes wavelength regions of visible light and excitation light as described above, and a rotation filter that includes a plurality of filters that selectively and mainly transmit light of each wavelength region. Also, the configuration of controlling the light emission of the plurality of light emitting elements that emit light of different wavelength regions as described above may also be utilized.

Also for the configuration of irradiating the light of each wavelength region in a time divisional manner, the motion specifying section 270 may specify the motion by using the image signal of any of color components at a plurality of timings, just as in the method described in relation to FIGS. 12 and 13. The subject image generating section 280 may generate an image of R signal that should be obtained at a timing other than the timing at which the light of the R wavelength region is not irradiated, based on the image of the R signal and the motion at the timing at which the light of the R wavelength region is being irradiated, for example. In the similar manner, the subject image generating section 280 may generate the image of the G signal at the timing at which the light of the G wavelength region is not being irradiated and the image of the B signal at the timing at which the light of the B wavelength region is not being irradiated. As a result, the subject image generating section 280 can generate a surface image of visible light that should be obtained at each timing.

Figure 14:
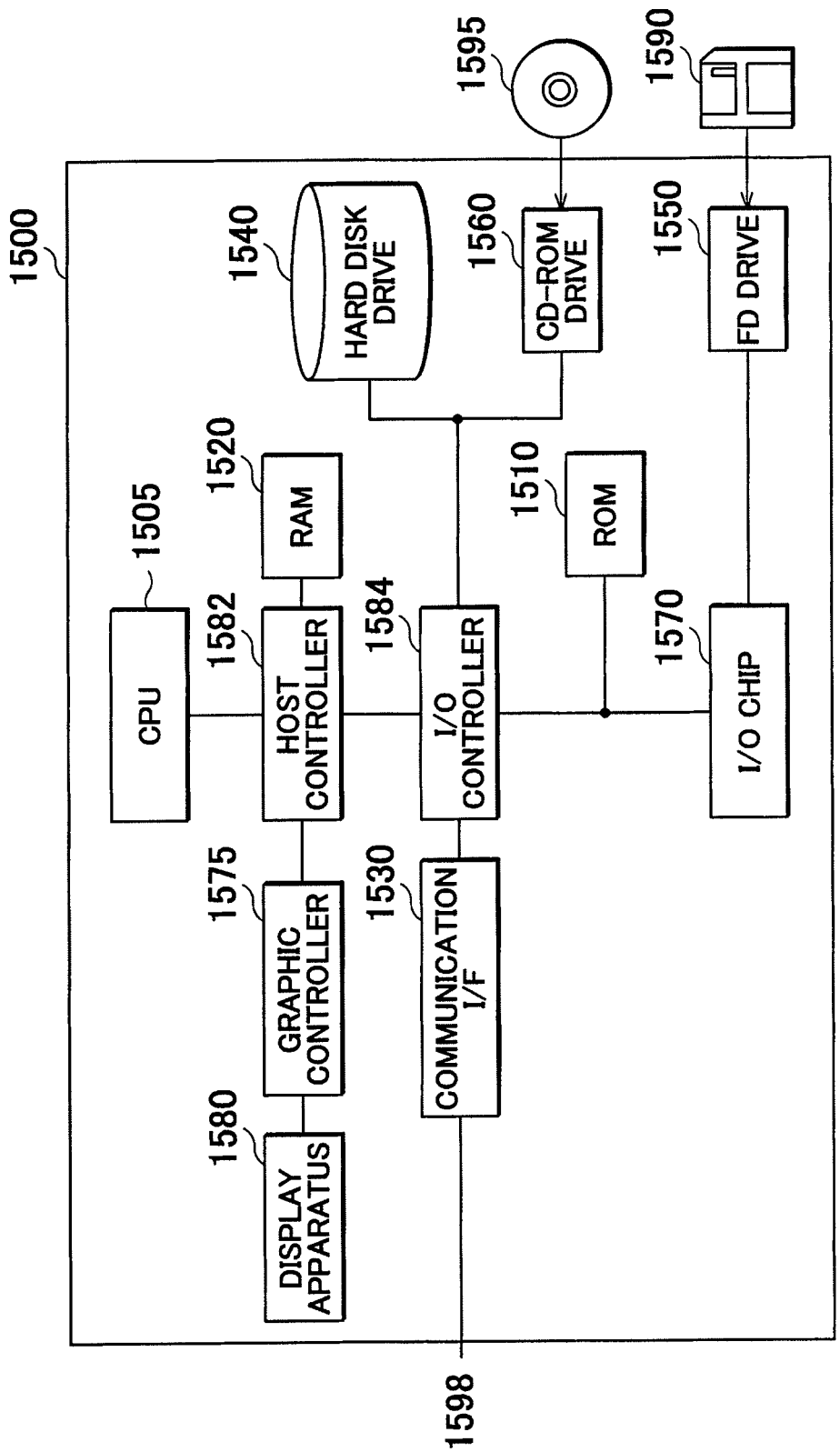
FIG. 14 shows an exemplary hardware configuration of the position specifying system 10 according to the present embodiment.

FIG. 14 shows an exemplary hardware configuration of a position specifying system 10 according to the present embodiment. The position specifying system 10 according to the present embodiment is provided with a CPU peripheral section, an input/output section, and a legacy input/output section. The CPU peripheral section includes a CPU 1505, a RAM 1520, a graphic controller 1575, and a display apparatus 1580 connected to each other by a host controller 1582. The input/output section includes a communication interface 1530, a hard disk drive 1540, and a CD-ROM drive 1560, all of which are connected to the host controller 1582 by an input/output controller 1584. The legacy input/output section includes a ROM 1510, a flexible disk drive 1550, and an input/output chip 1570, all of which are connected to the input/output controller 1584.

The host controller 1582 is connected to the RAM 1520 and is also connected to the CPU 1505 and the graphic controller 1575 accessing the RAM 1520 at a high transfer rate. The CPU 1505 operates to control each section based on programs stored in the ROM 1510 and the RAM 1520. The graphic controller 1575 obtains image data generated by the CPU 1505 or the like on a frame buffer provided inside the RAM 1520 and displays the image data in the display apparatus 1580. Alternatively, the graphic controller 1575 may internally include the frame buffer storing the image data generated by the CPU 1505 or the like.

The input/output controller 1584 connects the communication interface 1530 serving as a relatively high speed input/output apparatus, the hard disk drive 1540, and the CD-ROM drive 1560 to the host controller 1582. The communication interface 1530 communicates with other apparatuses via a network. The hard disk drive 1540 stores the programs and data used by the CPU 1505 in the image capturing system 10. The CD-ROM drive 1560 reads the programs and data from a CD-ROM 1595 and provides the read programs and data to the hard disk drive 1540 via the RAM 1520.

Furthermore, the input/output controller 1584 is connected to the ROM 1510, and is also connected to the flexible disk drive 1550 and the input/output chip 1570 serving as a relatively low speed input/output apparatus. The ROM 1510 stores a boot program executed when the image capturing system 10 starts up, a program relying on the hardware of the image capturing system 10, and the like. The flexible disk drive 1550 reads programs or data from a flexible disk 1590 and supplies the read programs or data to the hard disk drive 1540 via the RAM 1520. The input/output chip 1570 is connected to a variety of input/output apparatuses via the flexible disk drive 1550, and a parallel port, a serial port, a keyboard port, a mouse port, or the like, for example.

A communication program supplied to the hard disk drive 1540 via the RAM 1520 is provided by a user in a state where it is stored in a storage medium, such as the flexible disk 1590, the CD-ROM 1595, or an IC card. The communication program is read from the recording medium, installed via the RAM 1520 to the hard disk drive 1540 in the position specifying system 10, and is executed by the CPU 1505. The communication program installed to the position specifying system 10 to be executed acts on the CPU 1505 to cause the position specifying system 10 to function as each constituting element explained in FIGS. 1-13 included in the position specifying system 10. For example, the program causes the position specifying system 10 to function as the image capturing section 110, the image processing section 140, the output section 180, the light irradiation section 150, the control section 105, and the image processing section 140, explained with reference FIGS. 1-6.

Although some aspects of the present invention have been described by way of exemplary embodiments, it should be understood that those skilled in the art might make many changes and substitutions without departing from the spirit and the scope of the present invention which is defined only by the appended claims.

The operations, the processes, the steps, or the like in the apparatus, the system, the program, and the method described in the claims, the specification, and the drawings are not necessarily performed in the described order. The operations, the processes, the steps, or the like can be performed in an arbitrary order, unless the output of the former-described processing is used in the later processing. Even when expressions such as "First," or "Next," or the like are used to explain the operational flow in the claims, the specification, or the drawings, they are intended to facilitate the understanding of the invention, and are never intended to show that the described order is mandatory.

What is claimed is:

1. A position specifying system comprising:
    a light irradiation section that irradiates light to a first range and a second range of a physical body respectively;
    an image capturing section that captures images of an object existing inside the physical body, by means of the light irradiated to the first range and a second range; and
    a position specifying section that specifies a depth of the object from a surface of the physical body onto which the light from the light irradiation section is irradiated, based on a difference in the images captured by the image capturing section,
    wherein the position specifying section specifies that the depth is greater when a difference in at least one of an amount of blur, in a luminance value and in a contrast value between an image within the first range and an image within the second range of the object captured by means of the light irradiated at the first range is smaller.

2. The position specifying system according to claim 1, wherein
    the light irradiation section irradiates excitation light for exciting a luminescence substance within the object, and
    the image capturing section captures the images of the object by means of light emitted from the luminescence substance excited by the excitation light.

3. The position specifying system according to claim 1, wherein
    the image capturing section captures the images of the object by light emitted from the light irradiation section and reflected from the object.

4. The position specifying system according to claim 1, further comprising:
    an image correcting section that corrects an image of the object based on the depth specified by the position specifying section.

5. The position specifying system according to claim 4, wherein
    the image correcting section corrects spread of the image of the object based on the depth specified by the position specifying section.

6. The position specifying system according to claim 5, wherein
    the image correcting section corrects the spread of the image of the object which is caused by dispersion of light from the object between the object and a surface of the physical body.

7. The position specifying system according to claim 5, further comprising:
    a correction table that stores a correction value for correcting the spread of the image of the object, in association with the depth specified by the position specifying section, wherein the image correcting section corrects the spread of the image of the object, based on the correction value stored in the correction table and the depth specified by the position specifying section.

8. The position specifying system according to claim 4, further comprising:
a display control section that controls display of the image of the object after corrected by the image correcting section, according to the depth specified by the position specifying section.

9. The position specifying system according to claim 8, wherein
the display control section changes brightness or a color of the image of the object after corrected by the image correcting section, according to the depth specified by the position specifying section.

10. The position specifying system according to claim 1, wherein the position specifying section specifies that the depth is greater when a difference in at least one of an amount of blur, in a luminance value and in a contrast value between an image within the first range and an image within the second range of the object captured by means of the light irradiated at the second range is smaller.

11. The position specifying system according to claim 1, wherein
the image capturing section captures a first image of the object by means of the light irradiated to the first range and captures a second image of the object by means of the light irradiated to the second range, and
the position specifying section specifies that the depth is greater when a difference in at least one of an amount of blur, in a luminance value and in a contrast value between an image within the first range of the first image and an image within the first range of the second image is smaller.

12. The position specifying system according to claim 1, wherein the first range and the second range have an overlapped region.

13. The position specifying system according to claim 1, wherein the first range and the second range values of at least one of blur, luminance and contrast are determined from a common image captured by the image capturing section.

14. The position specifying system according to claim 12, wherein the first range is an image captured by the image capturing section with the light irradiation section illuminating the first range, and the position specifying section determines at least one of blur, luminance and contrast of the first range when the first range is illuminated in comparison with the first range when the light irradiation section illuminates the second range and the image is captured.

15. A position specifying method comprising:
irradiating light to a first range and a second range of a physical body respectively;
capturing images of an object existing inside the physical body, by means of the light irradiated to the first range and a second range; and
specifying a depth of the object from a surface of the physical body onto which the light is irradiated in the light irradiating, based on a difference in the images captured in the image capturing,
wherein the depth is greater when a difference in an amount of blur, in a luminance value or in a contrast value between an image within the first range and an image within the second range of the object captured by means of the light irradiated at the first range is smaller.

16. A non-transitory computer readable medium storing thereon a program for a position specifying system, the program causing the position specifying system to function as:
a light irradiation section that irradiates light to a first range and a second range of a physical body respectively;
an image capturing section that captures images of an object existing inside the physical body, by means of the light irradiated to the first range and a second range; and
a position specifying section that specifies a depth of the object from a surface of the physical body onto which the light from the light irradiation section is irradiated, based on a difference in the images captured by the image capturing section,
the position specifying section specifies that the depth is greater when a difference in an amount of blur, in a luminance value or in a contrast value between an image within the first range and an image within the second range of the object captured by means of the light irradiated at the first range is smaller.

* * * * *